United States Patent
Yamamoto et al.

(10) Patent No.: US 9,572,844 B2
(45) Date of Patent: Feb. 21, 2017

(54) IMMUNOSTIMULATION AGENT

(71) Applicant: NITTO PHARMACEUTICAL INDUSTRIES, LTD., Muko-shi, Kyoto (JP)

(72) Inventors: Kenji Yamamoto, Otsu (JP); Chiaki Matsuzaki, Kanazawa (JP); Keiko Hisa, Muko (JP)

(73) Assignee: Nitto Pharmaceutical Industries, Ltd., Muko (JP)

(*) Notice: Subject to any disclaimer, the term of this patent is extended or adjusted under 35 U.S.C. 154(b) by 0 days.

(21) Appl. No.: 14/768,665

(22) PCT Filed: Feb. 21, 2014

(86) PCT No.: PCT/JP2014/054233
§ 371 (c)(1),
(2) Date: Aug. 18, 2015

(87) PCT Pub. No.: WO2014/129599
PCT Pub. Date: Aug. 28, 2014

(65) Prior Publication Data
US 2015/0374762 A1 Dec. 31, 2015

(30) Foreign Application Priority Data
Feb. 22, 2013 (JP) ................. 2013-033072

(51) Int. Cl.
| | |
|---|---|
| *C12N 1/20* | (2006.01) |
| *A61K 39/02* | (2006.01) |
| *A61K 35/744* | (2015.01) |
| *A61K 35/74* | (2015.01) |
| *A61K 35/745* | (2015.01) |
| *A61K 35/747* | (2015.01) |
| *A61K 36/06* | (2006.01) |
| *C12R 1/01* | (2006.01) |
| *A61K 45/06* | (2006.01) |

(52) U.S. Cl.
CPC ............ *A61K 35/744* (2013.01); *A23K 10/18* (2016.05); *A23L 33/135* (2016.08); *A61K 35/74* (2013.01); *A61K 35/745* (2013.01); *A61K 35/747* (2013.01); *A61K 36/06* (2013.01); *A61K 45/06* (2013.01); *C12N 1/20* (2013.01); *C12R 1/01* (2013.01); *A23V 2002/00* (2013.01); *A23Y 2260/35* (2013.01)

(58) Field of Classification Search
None
See application file for complete search history.

(56) References Cited

U.S. PATENT DOCUMENTS

2013/0316032 A1 11/2013 Itoh et al.

FOREIGN PATENT DOCUMENTS

| | | |
|---|---|---|
| JP | 2007-308419 A | 11/2007 |
| JP | 2008-201708 A | 9/2008 |
| JP | 2010-057395 A | 3/2010 |
| JP | 2010-130954 A | 6/2010 |
| JP | 2012-158568 A | 8/2012 |
| WO | WO 99/12416 A1 | 3/1999 |
| WO | WO 99/16435 A1 | 4/1999 |
| WO | WO 2013/077500 A1 | 5/2013 |

OTHER PUBLICATIONS

Matsuzaki et al., "Properties of Lactic Acid Bacteria Isolated From Fresh Vegetables and Pickles," *Abstracts of the Annual Meeting of the Japan Society for Biosciences, Biotechnology and Agrochemistry*, Abstract 3A25a08 (Mar. 5, 2013).
Matsuzaki et al., "IgA-inducing Activity of *Leuconostoc mesenteroides* Isolated From Green Peas," *Abstracts of the Annual Meeting of the Society for Biotechnology*, Japan, 65: 207, Abstract 3P-078 (Aug. 25, 2013).
Matsuzaki et al, "Immunomodulating Activity of Exopolysaccharide-Producing *Leuconostoc mesenteroides* Strain NTM048 from Green Peas," *Journal of Applied Microbiology*, 116(4): 980-989 (2013).
Yasui et al., "The Study on Immunomodulatory Function and Preventive Function From Various Disease of Lactic Acid Bacteria Isolated from Traditional Fermented Foods," *Kenkyu Josei Katsudo Asahi Group Foundation—2004 Nendo Kenkyu Josei Hokoku* (2014) [retrieved from the Internet on May 12, 2014, at: URL: http://www.asahahibeerco.jp/csr.philanthropy/ab-academic/image/pdf/report2006/sci_04.pdf].
Japanese Patent Office, International Search Report in International Patent Application No. PCT/JP2014/054233 (May 20, 2014).
European Patent Office, Supplementary European Search Report for European Patent Application 14754913 (Jun. 24, 2016).

*Primary Examiner* — Jennifer Graser
(74) *Attorney, Agent, or Firm* — Leydig, Voit & Mayer, Ltd.

(57) ABSTRACT

The present invention provides *Leuconostoc mesenteroides* NTM048 strain deposited under accession No. NITE BP-1519, or a mutant strain thereof or a processed bacterium thereof, and a *lactobacillus* preparation and an immunity (particularly intestinal immunity) stimulant, containing the *lactobacillus* or a processed bacterium thereof.

15 Claims, 4 Drawing Sheets

SEQUENCE LISTING

<160> NUMBER OF SEQ ID NOS: 1

<210> SEQ ID NO 1
<211> LENGTH: 1516
<212> TYPE: DNA
<213> ORGANISM: Leuconostoc mesenteroides subsp. mesenteroides

<400> SEQUENCE: 1

```
agagtttgat cctggctcag gatgaacgct ggcggcgtgc ctaatacatg caagtcgaac      60
gcacagcgaa aggtgcttgc acctttcaag tgagtggcga acgggtgagt aacacgtgga     120
caacctgcct caaggctggg gataacattt ggaaacagat gctaataccg aataaaactt     180
agtgtcgcat gacacaaagt taaaaggcgc ttcggcgtca cctagagatg gatccgcggt     240
gcattagtta gttggtgggg taaaggccta ccaagacaat gatgcatagc cgagttgaga     300
gactgatcgg ccacattggg actgagacac ggcccaaact cctacgggag gctgcagtag     360
ggaatcttcc acaatgggcg aaagcctgat ggagcaacgc cgcgtgtgtg atgaaggctt     420
tcgggtcgta aagcactgtt gtatgggaag aacagctaga ataggaaatg attttagttt     480
gacggtacca taccagaaag ggacggctaa atacgtgcca gcagccgcgg taatacgtat     540
gtcccgagcg ttatccggat ttattgggcg taaagcgagc gcagacggtt tattaagtct     600
gatgtgaaag cccggagctc aactccggaa tggcattgga aactggttaa cttgagtgca     660
gtagaggtaa gtggaactcc atgtgtagcg gtggaatgcg tagatatatg gaagaacacc     720
agtggcgaag gcggcttact ggactgcaac tgacgttgag gctcgaaagt gtgggtagca     780
aacaggatta gataccctgg tagtccacac cgtaaacgat gaacactagg tgttaggagg     840
tttccgcctc ttagtgccga agctaacgca ttaagtgttc cgcctgggga gtacgaccgc     900
aaggttgaaa ctcaaaggaa ttgacgggga cccgcacaag cggtggagca tgtggtttaa     960
ttcgaagcaa cgcgaagaac cttaccaggt cttgacatcc tttgaagctt ttagagatag    1020
aagtgttctc ttcggagaca aagtgacagg tggtgcatgg tcgtcgtcag ctcgtgtcgt    1080
gagatgttgg gttaagtccc gcaacgagcg caacccttat tgttagttgc cagcattcag    1140
atgggcactc tagcgagact gccggtgaca aaccggagga aggcgggggac gacgtcagat    1200 catcatgccc cttatgacct gggctacaca cgtgctacaa tggcgtatac aacgagttgc    1260
caacccgcga gggtgagcta atctcttaaa gtacgtctca gttcggattg tagtctgcaa    1320
ctcgactaca tgaagtcgga atcgctagta atcgcggatc agcacgccgc ggtgaatacg    1380
ttcccgggtc ttgtacacac cgcccgtcac accatgggag tttgtaatgc ccaaagccgg    1440
tggcctaacc ttttaggaag gagccgtcta aggcaggaca gatgactggg gtgaagtcgt    1500
aacaaggtaa ccgtaa                                                    1516
```

IMMUNOSTIMULATION AGENT

CROSS-REFERENCE TO RELATED APPLICATIONS

This patent application is the U.S. national phase of International Patent Application No. PCT/JP2014/054233, filed Feb. 21, 2014, which claims the benefit of Japanese Patent Application No. 2013/033072, filed on Feb. 22, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 2,355 bytes ASCII (Text) file named "721654SequenceListing.txt," created Aug. 17, 2015.

TECHNICAL FIELD

The present invention relates to newly-isolated *lactobacillus* belonging to the genus *Leuconostoc*, an immunostimulant, particularly an intestinal immunostimulant, comprising the *lactobacillus* or a processed bacterium thereof, and the like. More particularly, the present invention relates to *Leuconostoc mesenteroides* NTM048 strain deposited under accession No. NITE BP-1519 or a processed bacterium thereof, having an IgA production promoting ability, and the like.

BACKGROUND ART

The intestinal immune organ is generically referred to as gut-associated lymphatic tissue (GALT), and mainly constituted of Peyer's patch, mesenteric lymph node and intestinal epithelium. Foreign substances (antigen) such as pathogens and the like that invaded the intestine are incorporated into M cells of Peyer's patch, and presented to T cells by antigen presenting cells such as dendritic cell and the like present in Peyer's patch. Simultaneously, B cells also recognize the antigen, and class switching from IgM$^+$ B cells to IgA$^+$ B cells occurs by cytokine stimulation to finally become plasma cells that secrete immunoglobulin A (hereinafter to be referred to as "IgA").

The number of intestine-specific IgA producing cells is about 70-80% of the plasma cells present in the whole body, and IgA secreted from the plasma cells afford infection defense such as inhibition of attachment of pathogens to the mucosal epithelial cells, neutralization of toxins and enzymes produced from pathogens by IgA binding thereto and the like. Therefore, it is highly important to activate intestinal immunity by IgA production to maintain balance of the immunity.

In recent years, the number of patients having allergic diseases is rapidly increasing. Such patients tend to show a decrease in the intestinal mucosal immunity, and therefore, the enhancement (development) of intestinal mucosal immunity is considered to highly possibility lead to the prophylaxis thereof.

As bacteria having an IgA production promoting ability and capable of enhancing intestinal immunity, *Lactobacillus plantarum* AYA strain (patent document 1), *Lactobacillus gasseri* strain (patent document 2) and the like have been reported.

*Lactobacillus* is isolated from various plants such as raw vegetable, pickles and the like and added to foods, drinks and the like as a probiotic. However, since reports of *lactobacillus* having an IgA production promoting ability and capable of activating the intestinal immunity are limited to the above-mentioned documents and the like, provision of a new *lactobacillus* having a high IgA production promoting ability has been desired.

DOCUMENT LIST

Patent Documents patent document 1: JP-A-2008-201708
patent document 2: JP-A-2010-130954

SUMMARY OF THE INVENTION

Problems to be Solved by the Invention

An object of the present invention is to isolate a novel *lactobacillus* a having an IgA production promoting ability, and provide an intestinal immunostimulant containing the strain or a processed bacterium thereof and the like.

Means of Solving the Problems

The present inventors have conducted intensive studies in view of the above-mentioned problem and found that a strain (NTM048) superior in IgA production promoting ability from about 200 strains of *lactobacillus* isolated from various raw vegetables and pickles, and identified that the strain is a new *lactobacillus* belonging to the genus *Leuconostoc*. Furthermore, the present inventors have found that the number of helper T cells in the spleen increases by the administration of the strain, and confirmed that the strain also affords not only the m intestinal immunity but also systemic immune system stimulating effect, which resulted in the completion of the present invention.

Therefore, the present invention provides the following.

[1] *Leuconostoc mesenteroides* NTM048 strain deposited under accession No. NITE BP-1519, or a mutant strain thereof or a processed bacterium thereof.
[2] A *lactobacillus* preparation comprising the strain of [1] or a processed bacterium thereof.
[3] The preparation of [2], which is an immunostimulant.
[4] The preparation of [2], which is an intestinal immunostimulant.
[5] The preparation of any of [2]-[4], further comprising other *lactobacillus* or a processed bacterium thereof, and/or a microorganism other than *lactobacillus* or a processed bacterium thereof.
[6] The preparation of [5], wherein the other *lactobacillus* is at least one kind selected from *Lactobacillus* bacteria, *Streptococcus* bacteria, *Leuconostoc* bacteria, *Pediococcus* bacteria, *Lactococcus* bacteria, *Enterococcus* bacteria and *Bifidobacterium* bacteria.
[7] The preparation of [5] or [6], wherein the microorganism other than *lactobacillus* is at least one kind selected from yeast, *Bacillus* bacteria, butyric acid bacteria (*Clostridium butyricum*) and fungi.
[8] The preparation of any of [2]-[7], which is used for prophylaxis or improvement of a disease relating to the intestinal immunity.
[9] The preparation of [8], wherein the disease relating to the intestinal immunity is selected from the group consisting of allergic diseases, infections, inflammatory bowel diseases and autoimmune diseases.

[10] The preparation of any of [2]-[9], which is a food or a food additive.

[11] The preparation of any of [2]-[9], which is a pharmaceutical product.

[12] The preparation of any of [2]-[9], which is a feed or a feed additive.

[13] A method of stimulating immunity in a warm-blooded animal, comprising administering an effective amount of *Leuconostoc mesenteroides* NTM048 strain, or a mutant strain thereof or a processed bacterium thereof to the mammal.

[14] *Leuconostoc mesenteroides* NTM048 strain or a mutant strain thereof or a processed bacterium thereof for use as an immunostimulant.

[15] Use of *Leuconostoc mesenteroides* NTM048 strain or a mutant strain thereof or a processed bacterium thereof, for the production of an immunostimulant.

Effect of the Invention

In the present invention, *lactobacillus* NTM048 strain newly isolated from pea has been clarified to have an IgA production promoting ability and a helper T cell increasing action. The present invention can provide a *lactobacillus* preparation and an immunity (particularly intestinal immunity) stimulant, containing the *lactobacillus* or a mutant strain thereof and a processed bacterium thereof. Since they can be used in various fields such as food and drink, pharmaceutical product, feed and the like, the present invention is industrially extremely useful.

BRIEF DESCRIPTION OF THE DRAWINGS

FIG. 1 shows the results of IgA production induction ability of *lactobacillus* NTM048 strain isolated in the present invention. In the Figure, the vertical axis shows the total IgA (ng/mL) in the culture supernatant, saline shows a negative control (added with saline alone), LPS shows a positive control (added with LPS), and the data shows mean±standard error (SE) of 6 different experiments. **$P<0.01$ (vs saline)

FIG. 5 shows the comparison results of the systemic immunity stimulating effect of NTM048 strain and JCM6124 strain. The upper panel shows the expression of CD4, CD8 in the spleen T lymphocytes of the mice in a control group (left), an NTM048 administration group (middle) and a JCM6124 administration group (right). In each Figure, the upper left box shows CD4 positive cells, the lower right box shows CD8 positive cells, the lower panel shows the ratio (%) of CD4 positive-CD3 positive cells in each group, and the data shows mean±standard error (SE).

DESCRIPTION OF EMBODIMENTS

The present invention is explained in detail below. The present invention provides a newly isolated *lactobacillus* (NTM048 strain) or a mutant strain thereof or a processed bacterium thereof, and a *lactobacillus* preparation or an immunostimulant (particularly the intestinal immunity) and the like containing any of these.

In the present invention, a new *lactobacillus* (NTM048 strain) was isolated from pea by the following method. The screening method and the bacteriological properties of NTM048 strain are as follows.

1. Screening
(1) Origin
   pea
(2) Screening Method
   Using a mouse Peyer's patch cell, screening was performed with enhancement of the IgA production as an index. Specific experimental procedures are as shown in the below-mentioned Examples.
2. Identification of *lactobacillus*
(1) *Leuconostoc mesenteroides* NTM048 Strain
(2) Visual Characteristics
   (2-1) White circular colony on MRS agar medium.
   (2-2) microscopic characteristics: coccus, no motility, spore is not formed.
(3) Growth Temperature
   Grows well at 30-37° C.
(4) Physiological, Biochemical Characteristics
   Gram staining: positive
   Sugar assimilability is shown in Table 1.

TABLE 1

| 0 | control | − |
|---|---|---|
| 1 | glycerol | − |
| 2 | erythritol | − |
| 3 | D-arabinose | − |
| 4 | L-arabinose | + |
| 5 | ribose | + |
| 6 | D-xylose | + |
| 7 | L-xylose | − |
| 8 | adonitol | − |
| 9 | β-methyl-D-xyloside | − |
| 10 | galactose | + |
| 11 | glucose | + |
| 12 | fructose | + |
| 13 | mannose | + |
| 14 | sorbose | − |
| 15 | rhamnose | − |
| 16 | dulcitol | − |
| 17 | inositol | − |
| 18 | mannitol | + |
| 19 | sorbitol | − |
| 20 | α-methyl-D-mannoside | − |
| 21 | α-methyl-D- | + |

TABLE 1-continued

| | | |
|---|---|---|
| | glucoside | |
| 22 | N-acetyl-glucosamine | + |
| 23 | amygdalin | + |
| 24 | arbutin | + |
| 25 | esculin | + |
| 26 | salicin | + |
| 27 | cellobiose | + |
| 28 | maltose | + |
| 29 | lactose | − |
| 30 | melibiose | + |
| 31 | saccharose | + |
| 32 | trehalose | + |
| 33 | inulin | − |
| 34 | melezitose | − |
| 35 | raffinose | + |
| 36 | starch | − |
| 37 | glycogen | − |
| 38 | xylitol | − |
| 39 | gentiobiose | + |
| 40 | D-turanosev | + |
| 41 | D-lyxose | − |
| 42 | D-tagatose | − |
| 43 | D-fucose | − |
| 44 | L-fucose | − |
| 45 | D-arabitol | − |
| 46 | L-arabitol | − |
| 47 | gluconate | + |
| 48 | 2-keto-gluconate | − |
| 49 | 5-keto-gluconate | + |

As chemical taxonomic properties, moreover, about 1.5 kb 16S rRNA is shown in SEQ ID NO: 1.

From the various properties above and in light of Bergey's Manual of Systematic Bacteriology, this strain was identified as a novel strain belonging to *Leuconostoc mesenteroides*, and named *Leuconostoc mesenteroides* NTM048. NTM048 strain was deposited on Jan. 25, 2013 at Incorporated Administrative Agency National Institute of Technology and Evaluation Patent Microorganisms Depositary, 2-5-8 Kazusakamatari, Kisarazu-shi, Chiba, Japan. The accession No. is NITE BP-1519.

The strain of the present invention also includes not only the above-mentioned NTM048 strain, but also a variant of the strain, which shows, at least in the gut-associated lymphatic tissue of mammals, an IgA production promoting action equal to or not less than that of NTM048 strain. The variant more preferably shows an IgA production promoting action in other organ and tissues (e.g., lung, bronchoalveolus, plasma etc.), and a helper T cell increasing action in the spleen, bone marrow, blood and the like, which are equal to or not less than those of NTM048 strain. Examples of a method of introducing mutation include, but are not limited to, a method by a chemical substance treatment such as a nitroso compound (nitrosoamine, nitrosoguanidine etc.), an alkylating agent (EMS; ethyl methanesulfonate), UV irradiation, radiation and the like. Whether the obtained mutant strain has an IgA production enhancing action in the gut-associated lymphatic tissues, which is equal to or not less than that of NTM048 strain, can be detected by measuring the IgA production promoting activity of the mutant strain according to a method similar to the method used for screening the above-mentioned NTM048, and comparing same with the activity of NTM048 strain.

In the present invention, NTM048 strain and a variant thereof can be cultivated using a medium for *lactobacillus* culture (solid medium, liquid medium etc.) such as the aforementioned MRS medium and the like.

The medium may contain various vitamins (vitamin A, vitamin B1, vitamin B2, vitamin B6, vitamin C, vitamin D, vitamin E etc., and derivatives thereof), various amino acids (including natural amino acid and synthetic amino acid), nucleic acid bases (purine, pyrimidine), inorganic salts ($MgSO_4$, $MnSO_4$, $FeSO_4$, NaCl etc.) and the like as necessary.

The strain of the present invention can be prepared by culturing at a culture temperature of 30-37° C., more preferably 35-37° C., for a culture period of 16 hr-3 days, more preferably 1-2 days, at pH 3-8, more preferably pH 4-7.

The processed bacteria of the present invention includes a culture medium obtained by the aforementioned method, and/or wet bacteria obtained by treating the culture medium by a method known per se, for example, centrifugation, filtration, magnetic separation and the like, or a washed product thereof (washing with sterilization water, PBS and the like is possible), freeze-dry powder thereof, heat-killed bacteria, dry-killed bacteria, chemical-killed bacteria, bacteria disrupture products such as bacterial wall and the like, an extract and the like.

In addition, fermentation products obtained by inoculating NTM048 strain or a mutant strain thereof itself to dairy product, cereals, processed food and the like are also included in the processed bacteria of the present invention.

In the present invention, the "immunostimulation" means an action to activate any immune function at least including intestinal immunity. Particularly, the immunostimulating action in the present invention is characterized by an action to promote IgA production in various organs, tissues, body fluids (e.g., lung, bronchoalveolus, plasma etc.) including gut-associated lymphatic tissues. In some cases, control of IgA production is also included in the concept of the immunostimulation in the present invention. Furthermore, the immunostimulating action of the strain of the present invention or a processed bacterium thereof includes activation of acquired immunity in the systemic immune system. The activation of acquired immunity in the systemic immune system is characterized by a helper T cell increasing action in the spleen, bone marrow, blood and the like.

Since NTM048 strain (also including the above-mentioned variant) and a processed bacterium thereof have an immunity (particularly intestinal immunity) stimulating action, they can be applied as immunity (particularly intestinal immunity) stimulants to human or other mammals directly or after formulating together with a suitable additive (*lactobacillus* preparation). Here, as the *lactobacillus* preparation, NTM048 strain (also including the above-mentioned variant) or a processed bacterium thereof can be used singly. It is also possible to use one or more kinds of other *lactobacillus* or processed bacterium thereof, and/or one or more kinds of microorganisms other than *lactobacillus* or processed bacteria thereof in combination. As used herein, the "processed bacteria" is as defined above.

Examples of other *lactobacillus* include, but are not limited to, *lactobacillus* belonging to the genus *Lactobacillus*, the genus *Streptococcus*, the genus *Leuconostoc*, the genus *Pediococcus*, the genus *Lactococcus*, the genus *Enterococcus*, the genus *Bifidobacterium* and the like.

Examples of microorganism other than *lactobacillus* include, but are not limited to, yeast, the genus *bacillus*, butyric acid bacteria (*Clostridium butyricum*), fungi such as koji bacteria and the like, and the like.

The NTM048 strain (also including variants) or a processed bacterium thereof of the present invention can be formulated by using these as active ingredients, and adding excipient, binder, disintegrant, lubricant and the like into a *lactobacillus* preparation or an immunity (particularly intestinal immunity) stimulant.

Examples of the additives that can be used for formulating include animal and plant oils such as soybean oil, safflower oil, olive oil, germ oil, sunflower oil, beef fat, sardine oil and the like, polyvalent alcohols such as polyethylene glycol, propylene glycol, glycerol, sorbitol and the like, surfactants such as sorbitan ester of fatty acid, sucrose ester of fatty acid, glycerin fatty acid ester, polyglycerol ester of fatty acid and the like, excipients such as purified water, lactose, starch, crystalline cellulose, D-mannitol, lecithin, gum arabic, sorbitol solution, carbohydrate solution and the like, binders such as hydroxypropylmethylcellulose, hydroxypropylcellulose, gelatin, pregelatinized starch, polyvinylpyrrolidone, polyvinyl alcohol and the like, disintegrants such as carmellose calcium, carmellose sodium, croscarmellose sodium, crospovidone, low-substituted hydroxypropylcellulose, cornstarch and the like, lubricants such as talc, hydrogenated vegetable oil, waxes, light anhydrous silicic acid and the like derived from naturally occurring substance and derivatives thereof, stearic acid, magnesium stearate, calcium stearate, aluminum stearate and the like, and the like.

The above-mentioned preparation can further contain a sweetener, a colorant, a pH adjuster, a flavor, various amino acids and the like. Also, tablet and granule may be coated by a well-known method. A liquid preparation may be dissolved or suspended in water or other suitable medium when in use.

As the number of bacterial NTM048 strains contained in the above-mentioned preparation, the daily ingestion amount is not less than $10^4$ colony forming units (hereinafter to be referred to as cfu) and not more than $10^{12}$ cfu, preferably not less than $10^6$ cfu and not more than $10^9$ cfu.

The aforementioned immunity (particularly intestinal immunity) stimulant can be applied to diseases relating to the intestinal immunity. Examples of the diseases relating to intestinal immunity include, but are not limited to, food (buckwheat, rice, wheat, egg, milk, peanut, fruits such as orange, apple, kiwi fruit and the like, crustaceans such as shrimp, crab and the like, shell and fish etc.) allergy, pollen (cedar, rice, hogweed, tall goldenrod, artemisia, Japanese white birch, timothy grass, orchard grass etc.) allergy, allergy to house dust, chemical substance, metal and the like, infections (bacterium infections such as *Staphylococcus aureus, Salmonella*, cholera, pathogenic *Escherichia coli, streptococcus mutans, clostridium*, dysentery *bacillus* and the like, virus infection such as influenza virus, rotavirus, norovirus, herpes virus and the like, parasitic insect infection, protozoa infection etc.), inflammatory bowel disease (Crohn's disease, ulcerative colitis etc.), autoimmune disease (organ-specific autoimmune disease and systemic autoimmune disease), functional degradation of intestinal immunity due to stress and the like.

The immunity (particularly intestinal immunity) stimulant of the present invention can be used for the prophylaxis or improvement of diseases relating to the intestinal immunity by administration to human or animals other than human (e.g., dog, cat, mouse, rat, hamster, guinea pig, rabbit, swine, bovine, chicken, parakeet, hill myna, goat, horse, sheep, monkey etc.).

Furthermore, the immunity (particularly intestinal immunity) stimulant of the present invention can be used as, for example, food, pharmaceutical product, feed and the like, or by adding the activator thereto.

When the immunity (particularly intestinal immunity) stimulant of the present invention is used as a food or a food additive, the form of the food is not particularly limited as long as it permits oral ingestion, such as solution, suspension, powder, solid formed article and the like. Specific examples include supplements (dispersion, granule, soft capsule, hard capsule, tablet, chewable tablet, quick-integrating tablet, syrup, liquid etc.), drinks (carbonic acid drink, lactic acid drink, sport drink, fruit juice drinks, vegetable drinks, soymilk beverage, coffee drinks, tea drinks, powder drinks, concentrated drinks, nutrition drinks, alcohol drinks etc.), dairy products (yogurt, butter, cheese, ice cream etc.), confectionery (gummy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage etc.).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

When the immunity (particularly intestinal immunity) stimulant of the present invention is used as a pharmaceutical product or pharmaceutical additive, the dosage form of the pharmaceutical product includes dispersion, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is prepared according to a conventional method.

Examples of the composition for oral administration include solid or liquid dosage form, specifically tablet (including sugar-coated tablet, film-coated tablet), pill, granule, powder, capsule (including soft capsule), syrup, emulsion, suspension and the like. Such compositions are produced by a known method, and may contain carrier, diluent or excipient generally used in the pharmaceutical field. As the carrier, excipient for tablet, lactose, starch, saccharose, magnesium stearate are used.

As a composition for parenteral administration, injection, suppository and the like are used. A preparation method of injection includes suspending or emulsifying the strain or a processed bacterium thereof of the present invention in an aseptic aqueous solution or oily solution generally used for injection. As an aqueous solution for injection, saline, isotonic solution containing glucose or other auxiliary agent and the like are used. As an oily solution, sesame oil, soybean oil and the like are used. A suppository for rectal administration can be prepared by mixing the strain of the present invention or a processed bacterium thereof with a general base for suppository.

When used as a pharmaceutical product, the immunity (particularly intestinal immunity) stimulant of the present invention may be used in combination with other medicament, for example, antiinflammatory agents, antibiotics, antivirus agents, anti-toxins, antiallergic agents and the like according to the target disease. The immunity (particularly the intestinal immunity) stimulant and the above-mentioned medicament of the present invention may be administered simultaneously or at different times to a subject.

Examples of a preferable concomitant drug for the immunity (particularly intestinal immunity) stimulant of the present invention include substances (prebiotics) that promote growth and/or metabolism of *lactobacillus* contained in the immunity (particularly intestinal immunity) stimulant. Such prebiotics can be added to the immunity (particularly intestinal immunity) stimulant of the present invention together with the strain of the present invention, or administered as a separate preparation simultaneously or at different times to a subject.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

When the intestinal tract-protecting agent of the present invention is used as a feed or a feed additive, the feed is, for example, pet food, stock raising or aquaculture feed additive and the like.

In the present invention, the IgA production can be measured by a method known per se. For example, Peyer's patch is prepared by the method using collagenase as shown in the below-mentioned Examples and the like, the Peyer's patch is cultured in the presence of *lactobacillus*, and the culture supernatant is recovered. The amount of IgA contained in the culture supernatant is measured by a method known per se such as the ELISA method (commercially available IgA measurement kit etc.) and the like. Thereafter, changes in the IgA amount are confirmed by comparing with a control group (e.g., saline as negative control, LPS etc. as positive control).

Peyer's patch can be selected irrespective of the kind thereof such as mouse, rat, human and the like and the production method thereof is not limited to the abovementioned methods and those of ordinary skill in the art can appropriately select them as necessary. Alternatively, to measure IgA production promoting activity in vivo, a biological sample (blood, feces etc.) can be collected from an individual (mouse, rat, human etc. irrespective of the kind), and changes in the IgA amount in the sample can be confirmed.

The present invention is explained in more detail in the following by referring to Examples. The Examples are mere exemplifications of the present invention and do not limit the scope of the present invention in any manner.

EXAMPLES

Reagents and Strains

RPMI-10 medium: RPMI 1640 medium (manufactured by Gibco) added with 10% fetal calf serum, MRS medium (manufactured by Difco), collagenase (manufactured by Sigma), DNase (manufactured by Takara)

NTM048 strain: isolated from pea (accession No.: KITE BP-1519, date of deposition: Jan. 25, 2013)

JCM16943 (*Leuconostoc mesenteroides* subsp. *cremoris*), JCM6124 (*Leuconostoc mesenteroides* subsp. *mesenteroides*): purchased from RIKEN, Tsukuba, BioResource Center, Japan Collection of Microorganism (JCM)

Reference Example 1

Preparation of Peyer's Patch Cell by Collagenase Production Method

Small intestine Peyer's patch cells were isolated from 7-week-old BALB/cA mouse. The cells were washed with RPMI-10 medium, transferred to a sterile dish containing 5 mL of IEC-dissociating solution (25 mM HEPES, 5 mM EDTA, 1 mM DTT in RPMI-10), and incubated in a $CO_2$ incubator at 37° C. for 45 min. After pipetting well, the cells were transferred to a sterile dish containing 5 mL of EDTA solution (5 mM EDTA in RPMI-10), and incubated in a $CO_2$ incubator at 37° C. for 5 min. After further pipetting well, the Peyer's patch was transferred to a 50 mL tube containing 5 mL of digestion solution (400 U/mL collagenase, 30 U/mL DNase in RPMI-10) and a stirrer, and incubated with stirring at 37° C. for 30 min. After completion of enzyme decomposition, Peyer's patch cells suspended in the medium were cloudy. They were centrifuged (1400 rpm, 7 min, 4° C.), and 4 mL of the supernatant was removed by suction. A suspension (1 mL) of the Peyer's patch cells was passed through a 40 µm cell strainer, centrifuged (1400 rpm, 7 min, 4° C.), the supernatant was removed by suction and suspended in 1 mL of RPMI-10 medium. The cells were counted, and used for the measurement of immune function activity.

Example 1

Measurement of IgA Production Amount

About 200 strains of *lactobacillus* isolated from various raw vegetables and pickles were investigated for the IgA production promoting ability by using mouse small intestine Peyer's patch cells.

Figure 1:
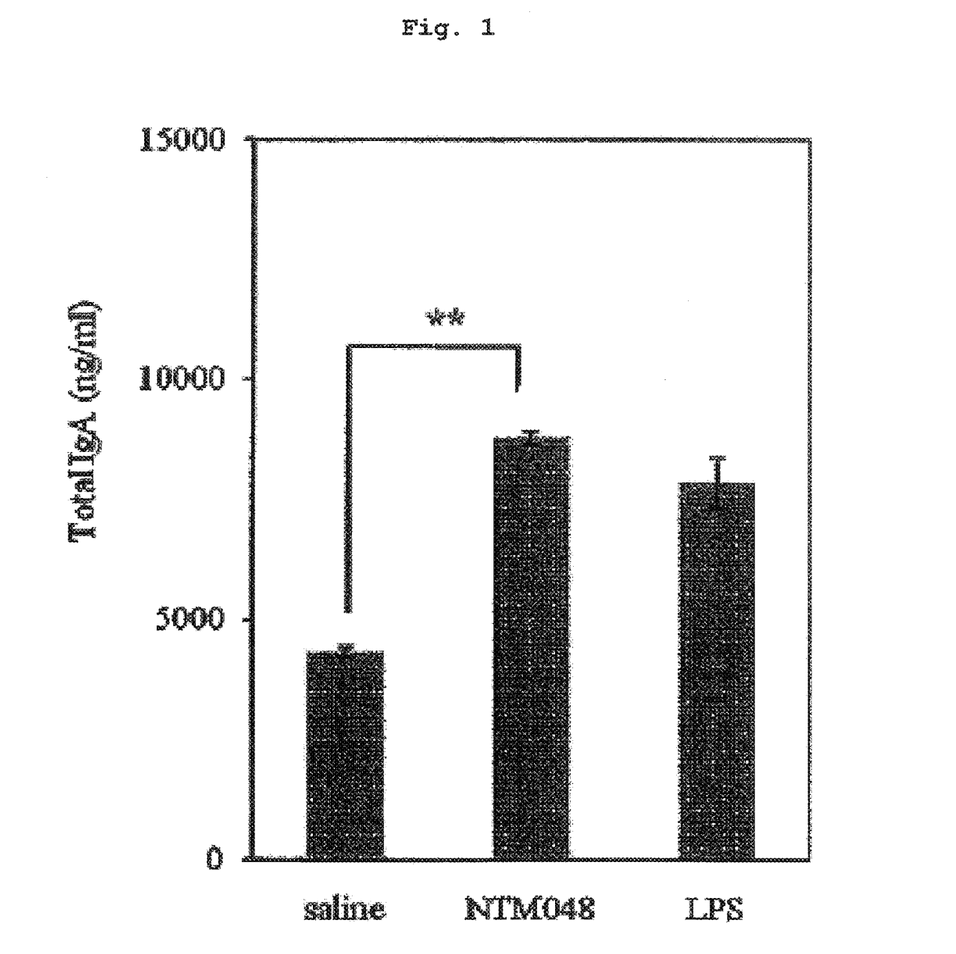

The concentration of Peyer's patch cells obtained by the aforementioned collagenase production method was adjusted to $2.5 \times 10^5$ cells/mL in a CD3 antibody-coated 96 well plate (manufactured by BD Biosciences). To the suspension of Peyer's patch cells was added an equal amount of *lactobacillus* having a concentration adjusted to 10 µg/mL with saline after liquid culture in MRS medium, and the mixture was reacted at 37° C. under 5% $CO_2$ anaerobic conditions for 5 days, and the total IgA amount produced was measured using Mouse IgA ELISA Quantitation Set (manufactured by BETHYL). Two strains of *lactobacillus* (NTM047, NTM048) having a significantly high IgA production ability were selected. The results of *lactobacillus* NTM048 strain are shown in FIG. 1.

The both NTM047, NTM048 strains were heat treated at 70° C. for 30 min, and the obtained killed bacteria were similarly examined for the IgA production ability by using Peyer's patch cells. As a result, the both strains were confirmed to have an IgA production promoting ability like that of living bacteria. The results suggest that IgA production promoting substances by NTM047 strain and NTM048 strain are bacterial walls or extra-bacterial components. Furthermore, species identification was tried by 16S rDNA sequence analysis. As a result, the both strains were clarified to be the same strains.

Example 2

Comparison with Type Strain

Figure 2:
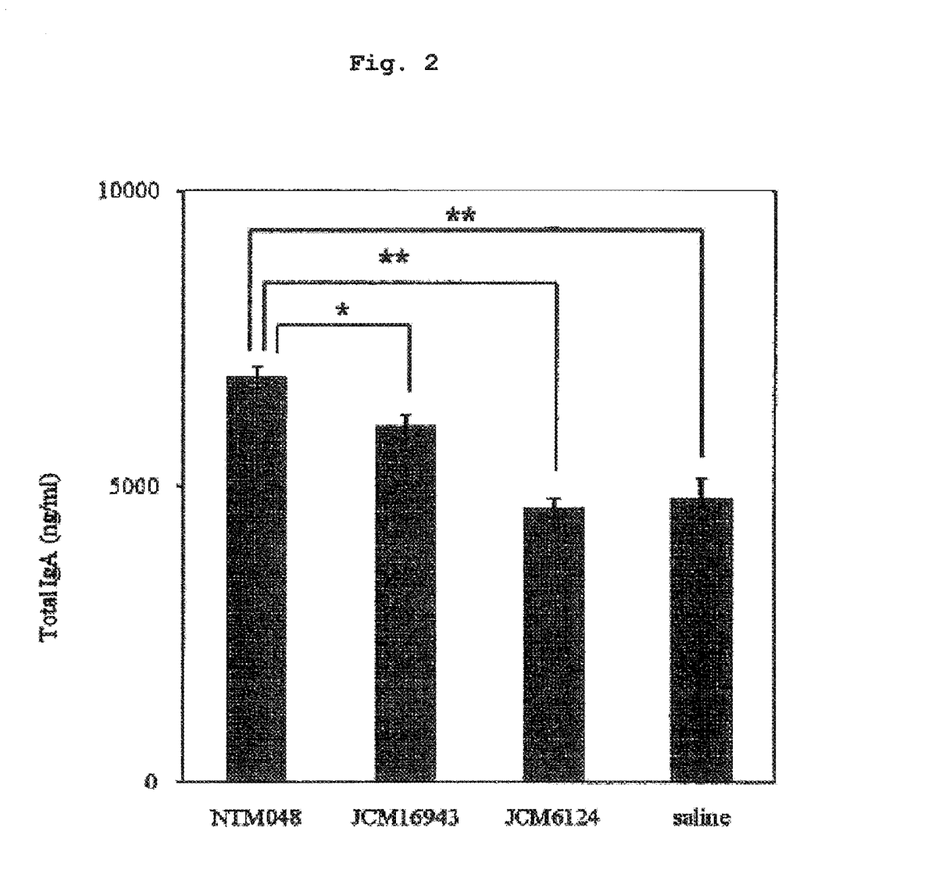
FIG. 2 shows the comparison results of the IgA production induction activity of NTM048 strain and other *Leuconostoc mesenteroides* strains (JCM16943 strain and JCM6124 strain). In the Figure, the vertical axis shows the total IgA (ng/mL) in the culture supernatant, saline shows a negative control (added with saline alone), and the data shows the mean±standard error (SE) of 6 different experiments. *$P<0.05$, **$P<0.01$ (vs saline)

By a method similar to that of Example 1, IgA production promoting activity in vitro was compared between NTM048 strain, and JCM16943 and JCM6124 by using Peyer's patch. The results are shown in FIG. 2.

NTM048 strain was confirmed to highly induce IgA production as compared to other strains of *Leuconostoc mesenteroides*.

Example 3

Confirmation of IgA Production Promoting Activity In Vivo

6-Week-old male BALB/c mice were preliminarily reared (*lactobacillus*-free feed; AIN-76) for 2 weeks, AIN-76 containing 0, 0.05, 0.5, 5% *lactobacillus* NTM048 was administered to 5 mice in each test group for 2 weeks, the feces was collected on days 0, 7, 14 and IgA amount was confirmed. After collection, the feces was freeze-dried for 6 hr, and suspended at a ratio of feces weight 10 mg/200 μL in an extraction buffer (PBS) containing Protease Inhibitor Cocktail (manufactured by Roche). The suspension was stirred by vortex, ice-cooled for 30 min, centrifuged (15000 rpm, 10 min, 4° C.), and the total IgA amount extracted into the supernatant was measured by the ELISA method as mentioned above.

Figure 3:
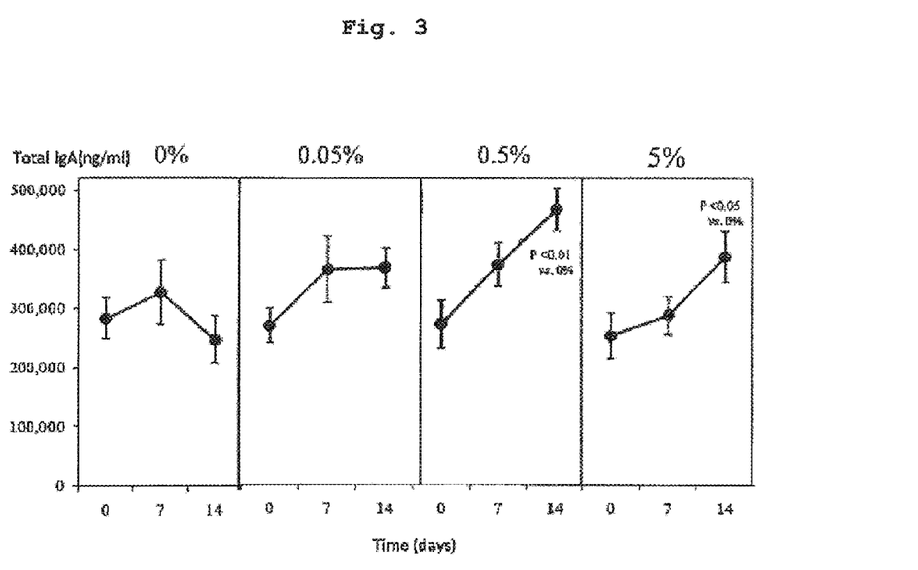
FIG. 3 shows IgA production inducing activity when feeds containing NTM048 strain at various compositions (numerical value on each graph shows NTM048 concentration) were orally administered to mouse. In the Figure, the vertical axis shows Total IgA (ng/mL) in a feces extract, and the horizontal axis shows the number of days of administration, and the data shows mean±standard error (SE) of an experiment per 5 mice in the test section.

The composition of the feed is shown in Table 2, and the results of IgA production promotion are shown in FIG. 3.

TABLE 2

| test group | feed composition (%) | | feed composition (g) | | | | CFU/g (feed) |
|---|---|---|---|---|---|---|---|
| | bacteria (%) | bacterial body (%) | AIN-76 | bacteria | dispersing medium | total | |
| 1 | 0 | 0 | 95 | 0 | 5 | 100 | 0 |
| 2 | 0.05 | 0.0038 | 95 | 0.05 | 4.95 | 100 | $7.1 \times 10^8$ |
| 3 | 0.5 | 0.038 | 95 | 0.5 | 4.5 | 100 | $7.1 \times 10^9$ |
| 4 | 5 | 0.38 | 95 | 5 | 0 | 100 | $7.1 \times 10^{10}$ |

On day 14, the IgA amount increased in all bacteria administration groups, and a significant difference (P<0.01, P<0.05) was found in 0.5% and 5% NTM048 strain administration mice.

Example 4

Comparison with Type Strain in IgA Production Promoting Activity In Vivo

Figure 4:
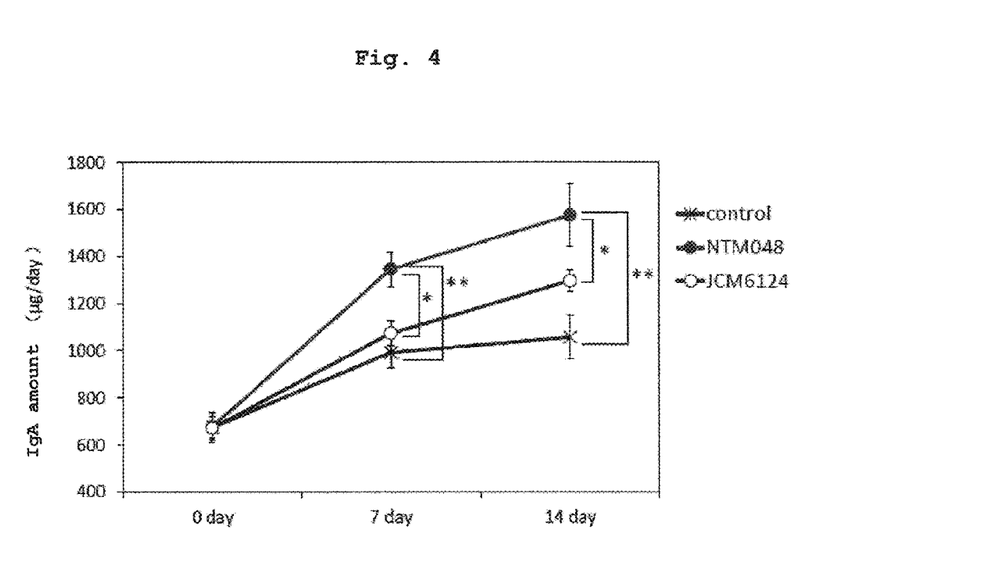
FIG. 4 shows the comparison results of the IgA production induction activity in the intestinal mucosa of NTM048 strain and JCM6124 strain in vivo. In the Figure, the vertical axis shows the IgA amount (μg/day) in one day's feces, and the horizontal axis shows the number of days of administration, and control shows a negative control (administered with AIN-76 containing dispersing medium alone (0.05% (w/w))). *$P<0.05$ (vs JCM6124), **$P<0.01$ (vs control)

6-Week-old male BALB/c mice were preliminarily reared (*lactobacillus*-free feed; AIN-76) for 2 weeks, AIN-76 containing 0.0038% (w/w) NTM048 strain or JCM6124 strain based on freeze-dried bacteria were administered to 6 mice in each test group for 2 weeks, the feces for 24 hr was collected on days 0, 7, 14 and the weight after freeze-drying was measured to determine daily amount of feces. The feces was pulverized in a mortar, freeze-dried again, 50 mg was dispensed to an Eppendorf tube, and suspended at a ratio of feces weight 10 mg/200 μL in an extraction buffer (PBS) containing Protease Inhibitor Cocktail (manufactured by Roche). After stirring by vortex, the feces was stirred again by vortex every 10 min, placed on ice and, after 30 min, centrifuged at 4° C., 15000 rpm for 10 min and the supernatant was recovered. The concentration of IgA in the supernatant was measured by the ELISA method as mentioned above, and the IgA amount in one day's feces was determined from the obtained IgA concentration and the weight of feces for 24 hr. The results are shown in FIG. 4.

NTM048 strain was confirmed to also highly induce IgA production in vivo in the intestinal mucosa as compared to JCM6124 strain.

Example 5

Analysis of T Cell Subtype in Mouse Spleen Cell

To examine an influence of NTM048 strain administration on the systemic immune system, T cell subtypes in spleen cells were compared.

NTM048 strain or JCM6124 strain was administered to mouse for 3 weeks, and the spleen was isolated. A spleen cell suspension was prepared by suspending spleen cells physically collected using an injection needle in RPMI 10 medium, treating same with a hemolysis buffer (0.83% $NH_4Cl$, 0.1% $KHCO_3$, 0.0037% EDTA2Na) for 5 min, washing same with RPMI 10 medium, and passing same through a 70 μm cell strainer. Using spleen cells at $1 \times 10^6$ cells, CD4, CD8 subtype analysis of T cells was performed. Using Mouse T Lymphocyte Subset Antibody Cocktail (BD Biosciences) and according to the product protocol, the cells were labeled with PE-Cy™7-labeled anti-CD3e antibody, PE-labeled anti-CD4 antibody and APC-labeled anti-CD8a antibody, and CD3 positive cells (T cells), CD4 positive cells (helper T cells), and CD8 positive cells (killer T cells) were measured by a flow cytometer (BD FACSAria). The results are shown in FIG. 5.

Figure 5:
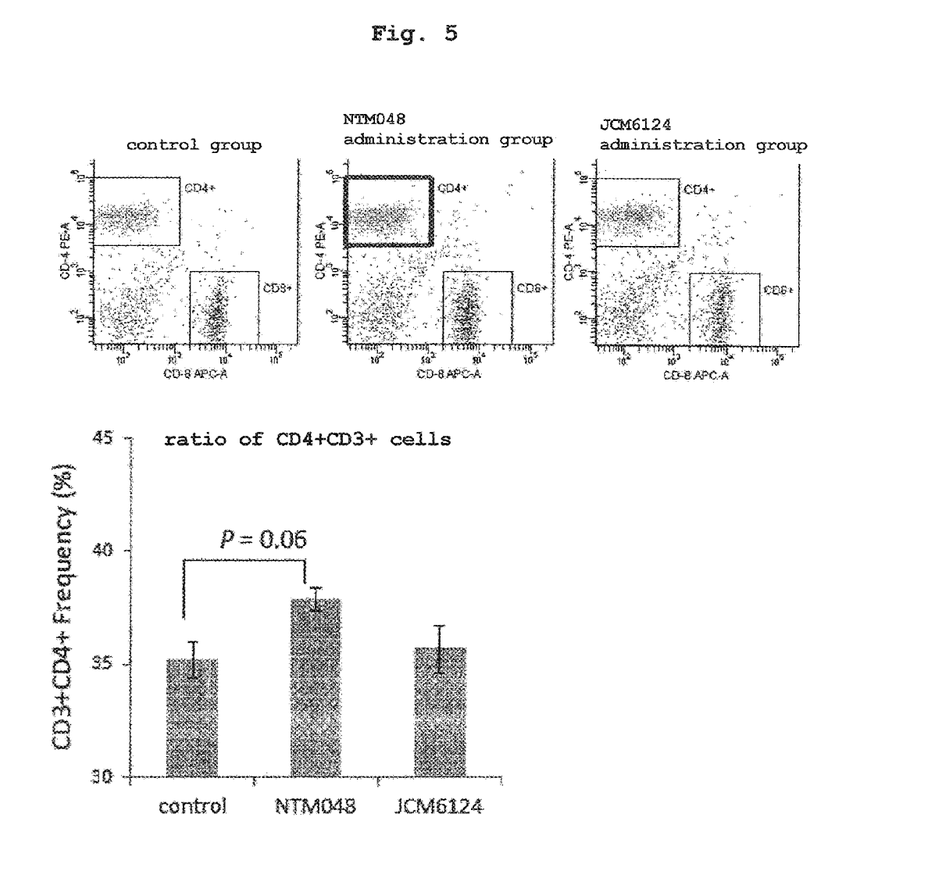

The ratio of CD8 positive and CD3 positive cells did not show a significant difference between any of *lactobacillus* administration groups and control group (FIG. 5, top), and the ratio of CD4 positive and CD3 positive cells tended to increase as compared to the control group (p=0.06) and JCM6124 administration group (FIG. 5 top, bottom). These results suggest that the immunity stimulating effect of NTM048 strain can be also expected in the systemic immunity (particularly acquired immunity) system.

INDUSTRIAL APPLICABILITY

The present invention clarified that a newly isolated and identified *lactobacillus* (NTM048 strain) has a high IgA production promoting ability. The strain, a processed bacterium thereof and the like have a high IgA production promoting ability, and can be applied to various fields such as pharmaceutical product, food, feed and the like. Therefore, the present invention is industrially extremely useful.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

This application is based on a patent application No. 2013-033072 filed in Japan on Feb. 22, 2013, the contents of which are incorporated in full herein by reference.

The invention claimed is:

1. A method of stimulating immunity in a mammal, comprising administering to the mammal an effective amount of *Leuconostoc mesenteroides* NTM048 strain deposited under Accession No. NITE BP-1519, a culture medium thereof, wet bacteria thereof, a washed product thereof, freeze-dry powder thereof, heat-killed bacteria thereof, dry-killed bacteria thereof, chemical-killed bacteria thereof, bacteria disrupture product thereof or fermentation product obtained by inoculating NTM048 strain.

2. The method according to claim 1, wherein the *Leuconostoc mesenteroides* NTM048 strain, a culture medium thereof, wet bacteria thereof, a washed product thereof, freeze-dry powder thereof, heat-killed bacteria thereof, dry-killed bacteria thereof, chemical-killed bacteria thereof, bacteria disrupture product thereof or fermentation product obtained by inoculating NTM048 strain is administered in a *lactobacillus* preparation to the mammal.

3. The method according to claim 2, wherein the *lactobacillus* preparation is a food or a food additive.

4. The method according to claim 2, wherein the *lactobacillus* preparation is a pharmaceutical composition.

5. The method according to claim 2, wherein the *lactobacillus* preparation is a feed or a feed additive.

6. The method according to claim 2, wherein the *lactobacillus* preparation further comprises other *lactobacillus*, a culture medium thereof, wet bacteria thereof, a washed product thereof, freeze-dry powder thereof, heat-killed bacteria thereof, dry-killed bacteria thereof, chemical-killed bacteria thereof, bacteria disrupture product thereof, an extract thereof or fermentation product obtained by inoculating the *lactobacillus*.

7. The method according to claim 6, wherein the other *lactobacillus* is at least one kind selected from the group consisting of *Lactobacillus* bacteria, *Streptococcus* bacteria, *Leuconostoc* bacteria, *Pediococcus* bacteria, *Lactococcus* bacteria, *Enterococcus* bacteria and *Bifidobacterium* bacteria.

8. The method according to claim 2, wherein the *lactobacillus* preparation further comprises a microorganism other than *lactobacillus*, a culture medium thereof, wet bacteria thereof, a washed product thereof, freeze-dry powder thereof, heat-killed bacteria thereof, dry-killed bacteria thereof, chemical-killed bacteria thereof, bacteria disrupture product thereof, an extract thereof or fermentation product obtained by inoculating the *lactobacillus*.

9. The method according to claim 8, wherein the microorganism other than *lactobacillus* is at least one kind selected from the group consisting of yeast, *Bacillus* bacteria, butyric acid bacteria and fungi.

10. The method according to claim 2, wherein the *lactobacillus* preparation further comprises (a) other *lactobacillus*, a culture medium thereof, wet bacteria thereof, a washed product thereof, freeze-dry powder thereof, heat-killed bacteria thereof, dry-killed bacteria thereof, chemical-killed bacteria thereof, bacteria disrupture product thereof, an extract thereof or fermentation product obtained by inoculating the *lactobacillus* and (b) a microorganism other than *lactobacillus*, a culture medium thereof, wet bacteria thereof, a washed product thereof, freeze-dry powder thereof, heat-killed bacteria thereof, dry-killed bacteria thereof, chemical-killed bacteria thereof, bacteria disrupture product thereof, an extract thereof or fermentation product obtained by inoculating the microorganism.

11. The method according to claim 10, wherein (a) the other *lactobacillus* is at least one kind selected from the group consisting of *Lactobacillus* bacteria, *Streptococcus* bacteria, *Leuconostoc* bacteria, *Pediococcus* bacteria, *Lactococcus* bacteria, *Enterococcus* bacteria and *Bifidobacterium* bacteria, and (b) the microorganism other than *lactobacillus* is at least one kind selected from the group consisting of yeast, *Bacillus* bacteria, butyric acid bacteria and fungi.

12. The method according to claim 2, wherein the mammal has a disease relating to intestinal immunity.

13. The method according to claim 12, wherein the disease relating to intestinal immunity is selected from the group consisting of allergic diseases, infections, inflammatory bowel diseases, and autoimmune diseases.

14. The method according to claim 9, wherein the butyric acid bacteria is *Clostridium butyricum*.

15. The method according to claim 11, wherein the butyric acid bacteria is *Clostridium butyricum*.

\* \* \* \* \*